United States Patent
Lopez et al.

(10) Patent No.: US 7,465,381 B2
(45) Date of Patent: Dec. 16, 2008

(54) ELECTROKINETIC MOLECULAR SEPARATION IN NANOSCALE FLUIDIC CHANNELS

(75) Inventors: Gabriel P. Lopez, Albuquerque, NM (US); Steven R. J. Brueck, Albuquerque, NM (US); Linnea K. Ista, Albuquerque, NM (US); Anthony L. Garcia, Albuquerque, NM (US); Dimiter N. Petsev, Albuquerque, NM (US); Paul Bisong, Albuquerque, NM (US); Michael J. O'Brien, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 441 days.

(21) Appl. No.: 10/958,113

(22) Filed: Oct. 4, 2004

(65) Prior Publication Data
US 2006/0169587 A1    Aug. 3, 2006

Related U.S. Application Data

(60) Provisional application No. 60/589,200, filed on Jul. 19, 2004, provisional application No. 60/538,862, filed on Jan. 22, 2004.

(51) Int. Cl.
*G01N 27/447* (2006.01)
(52) U.S. Cl. ............... 204/451; 204/450; 977/924; 977/962
(58) Field of Classification Search ......... 204/450–455, 204/600–605
See application file for complete search history.

(56) References Cited

U.S. PATENT DOCUMENTS

| | | |
|---|---|---|
| 3,855,133 A | 12/1974 | Roehsler |
| 4,801,380 A | 1/1989 | Parker et al. |
| 4,814,082 A | 3/1989 | Wrasidlo |
| 4,814,088 A | 3/1989 | Kutowy et al. |
| 4,902,424 A | 2/1990 | Wrasidlo |
| 4,935,141 A | 6/1990 | Buck et al. |
| 4,969,998 A | 11/1990 | Henn |
| 5,013,337 A | 5/1991 | Bedard et al. |
| 5,019,263 A | 5/1991 | Haag et al. |
| 5,130,025 A | 7/1992 | Lefebvre et al. |
| 5,145,584 A | 9/1992 | Swamikannu |
| 5,266,207 A | 11/1993 | Boye et al. |
| 5,302,264 A * | 4/1994 | Welch et al. ............. 204/452 |
| 5,474,675 A | 12/1995 | Kupka |
| 5,716,527 A | 2/1998 | Deckman et al. |
| 5,723,031 A * | 3/1998 | Durr et al. ............. 204/451 |
| 5,753,014 A | 5/1998 | Van Rijn |
| 5,798,042 A | 8/1998 | Chu et al. |

(Continued)

OTHER PUBLICATIONS

Klett et al. (Analytical Chemistry, 2001, 73, pp. 1909-1915).*

(Continued)

*Primary Examiner*—Alex Noguerola
(74) *Attorney, Agent, or Firm*—Schwegman, Lundberg & Woessner, P.A.

(57) ABSTRACT

A method for separation of mixtures in fluidic systems through electrokinetic transport by use of nanochannels when the fluidic systems approach the size of an electrical double layer, thereby allowing separation based on charge. The disclosed apparatus comprises a T-chip with a nanochannel section. The method and apparatus are useful for separation of many molecular species, including peptides, proteins, and DNA.

22 Claims, 5 Drawing Sheets

U.S. PATENT DOCUMENTS

| | | | |
|---|---|---|---|
| 5,876,830 A | 3/1999 | Michl et al. | |
| 5,938,923 A | 8/1999 | Tu et al. | |
| 5,993,661 A | 11/1999 | Ruckenstein et al. | |
| 6,043,177 A | 3/2000 | Falconer et al. | |
| 6,044,981 A | 4/2000 | Chu et al. | |
| 6,051,517 A | 4/2000 | Funke et al. | |
| 6,060,415 A | 5/2000 | Chao et al. | |
| 6,090,289 A | 7/2000 | Verduijn et al. | |
| 6,100,393 A | 8/2000 | Lopez Ortiz et al. | |
| 6,113,794 A | 9/2000 | Kumar et al. | |
| 6,113,795 A | 9/2000 | Subramaniam et al. | |
| 6,177,373 B1 | 1/2001 | Sterte et al. | |
| 6,190,638 B1 | 2/2001 | Anthonis et al. | |
| 6,243,348 B1 | 6/2001 | Goodberlet | |
| 6,264,044 B1 | 7/2001 | Meyering et al. | |
| 6,296,752 B1 | 10/2001 | McBride et al. | |
| 6,361,671 B1 | 3/2002 | Mathies et al. | |
| 6,368,871 B1 | 4/2002 | Christel et al. | |
| 6,685,841 B2 | 2/2004 | Lopez et al. | |
| 7,220,345 B2 * | 5/2007 | Bohn et al. | 204/600 |
| 2004/0262159 A1 * | 12/2004 | Martin et al. | 204/450 |

OTHER PUBLICATIONS

Wang et al. (Analytical Chemistry, 1999, 71, pp. 3901-3904).*

Vandaveer IV et al. (Electrophoresis, 2002, 23, pp. 3667-3677).*

* cited by examiner

ELECTROKINETIC MOLECULAR SEPARATION IN NANOSCALE FLUIDIC CHANNELS

CROSS-REFERENCE TO RELATED APPLICATIONS

The Applicant claims priority to a Provisional Application filed Oct. 2, 2003 Ser. No. 60/508,703, to a Provisional Application filed on Jan. 22, 2004, Ser. No. 60/538,862, and to a Provisional Application filed on Jul. 19, 2004, Ser. No. 60/589,200.

STATEMENT REGARDING FEDERALLY SPONSORED RESEARCH

The invention was made with U.S. Government support under Grant No. CTS-0304237, awarded by the National Science Foundation. As a result, the U.S. Government has certain rights in this invention.

BACKGROUND OF THE INVENTION

1. Field of the Invention

The present invention involves transport of complex fluids in channels of nanoscale dimension. More particularly, it examines efficient separation of biomolecular components within complex mixtures, including protein separations.

2. Description of the State of the Art

As nanofluidic devices receive increasing attention, elucidation of phenomena associated with flow of liquids through conduits of nanoscale dimensions remains an important scientific goal. Specifically, the development of chip-based nanofluidic systems for molecular separations (See K. P. Travis, et al., *Physical Review E* 55 4288 (1997); L. A. Pozhar, K. E. Gubbins, *Journal of Chemical Physics* 99 8970 (1993)), especially of biomolecular mixtures, based on nanoscale phenomena including entropic trapping (See J. Han, S. W. Turner, H. G. Craighead, *Physical Review Letters* 86 1394 (1999)), and shear-driven chromatography (See D. Clicq, et al., *Journal of Chromatography* 979 33 (2002); C. W. Huck, G. Stecher, R. Bakry, G. K. Bonn, *Electrophoresis* 24 3977 (2003)), has recently received intense interest. In addition to a limited number of experimental efforts (See S. C. Jacobson, J. P. Alarie, J. M. Ramsey, in *Proceedings of Micro Total Analysis Systems* 2001, Dordrecht, The Netherlands, 57-59 (2001); R. Karlsson, et al., *Langmuir* 18 4186 (2002); D. Stein, M. Kruithof, C. Dekker, *Physical Review Letters* 93 035901 (2004)), several important theoretical studies have sought to clarify the effects of nanoconfinement of fluid flows on the molecular distributions and trajectories in electrokinetic flows (See B. J. Loughnane, et al., *Journal of Physical Chemistry B* 104 5421 (2000); P. J. Kemery, et al., *Langmuir* 14 2884 (1998); A. P. Thompson, *J. Chem. Phys.* 119 7503 (2003); Q. S. Pu, J. S. Yun, H. Temkin, S. R. Liu, *Nano Letters* 4 1099 (2004)). For example, a recent study concluded that effects resulting from the non-continuum nature of electrokinetic flows in nanoscopic pores are associated with varying fluid viscosity very close to the pore wall (See R. Qiao, N. R. Aluru, *J. Chem. Phys.* 118 4692 (2003)). Further, it was found that with this correction, electroosmotic velocity profiles away from solid surfaces, after a few molecular layers, are in reasonable accordance with the previously elucidated continuum theory (See C. L. Rice and R. Whitehead, *J. Phys. Chem.* 69 4017(1965); R. J. Hunter, *Zeta potential in colloid science: principles and applications*. (Academic Press: London, 1981)). Thus far, theoretical investigation of the effects of nanoconfinement on electrokinetic transport of fluids has outpaced experiments because the details of such fluid flows have been unobservable by standard near- and far-field techniques.

Therefore, there has been a long-felt need in the art to (1) develop methodologies for investigation of electrokinetic transport in nanoscale channels using confocal scanning laser microscopy (CSLM), a widely available far field technique; (2) show how data obtained can be compared with analytical models for fluid transport within very small channels; and (3) explore the potential for the use of nanoconfined electrokinetic transport in the development of new methodologies for molecular separation.

With this in mind, one should understand that polyacrylamide gel electrophoresis (PAGE) remains the standard for biomolecular separation and identification in biotechnology. Nevertheless, the set of separation strategies that rely on this technique are hampered by (1) inconvenience and irreproducibility in preparation of the variety of gels needed for the separations, (2) limited resolution and dynamic range of biomolecular separations, (3) susceptibility of the polymer to degradation under high electric fields, (4) limitations in their compatibility with mass spectrometric identification of proteins and (5) relatively large volumes and concentrations of material needed for detection of separated species. Gradient PAGE techniques are recognized to have good resolution and dynamic range, but their utility is greatly hampered by the need for cumbersome gel synthesis protocols and lack of reproducibility.

Previous work on nanofluidic bioseparation systems has included the development of Brownian ratchets (See A. van Oudenaarden et al., Brownian ratchets: Molecular separations in lipid bilayers supported on patterned arrays", *Science*, 285, 1046-1048 (1999); C. F. Chou, et al., Sorting by diffusion: An asymmetric obstacle course for continuous molecular separation", *Proc. Natl. Acad. Sci. USA*, 96, 13762-13765 (1999)), and entropic traps (See J. Han et al., Separation of long DNA molecules in a microfabricated entropic trap array, *Science*, 288, 1025, 1029 (2000)), that achieved efficient separation of biomolecules, albeit at rates that cannot be considered commensurate with high throughput technologies. While providing important insight into the behavior of transport of individual molecules (especially DNA) through tortuous nanofluidic systems, these demonstrations have not led to a widespread use of such systems by the biotechnological community. The primary reasons for this is the difficulty by which the nanofluidic systems have been prepared, the high costs of fabrication, and the inability of the fabrication techniques to produce macroscopic arrays of nanofluidic pathways of specified, predetermined, functional design. A primary contribution of this project to the biotechnological world will be to overcome these obstacles by introducing interferometric lithography (IL) as the nanofabrication tool of choice in the fabrication of nanofluidic systems for large scale bioseparations.

To date, the majority of nanofluidic systems have been developed primarily for separation of nucleic acids, while similar systems for separation of other biomolecules lay far behind. Increasingly, microfluidic devices are being developed that have direct application to the burgeoning field of proteomics. (See G. J. M. Bruin, Recent developments in electrokinetically driven analysis on microfabricated devices, *Electrophoresis*, 21, 3931-3951 (2000)). Analysis of the protein composition of organisms, tissues and single cells under a variety of physiological and environmental conditions is expanding not only our basic understanding of biomolecular function (See N. Anderson, et al., Proteomics: applications in basic and applied biology, *Current Opinion in Biotechnology*, 11, 408-412 (2000)), but is also showing promise for diverse and tangible rewards in areas such as but not limited to drug discovery (See J. H. Wang et al., Proteomics in drug discovery, *Drug Discovery Today*, 4, 129-133 (1999)), rapid diagnosis and treatment of disease, and rapid development of vaccines (See R. Aebersold et al., Mass spectrometry in proteomics, *Chemical Reviews*, 101, 269-295 (2001)), the latter of which is of particular contemporary importance. Proteomic analysis is relying increasingly on precise separation of proteins coupled with the sensitive detection and analysis capabilities of mass spectrometry (See G. Grandi, Antibacterial vaccine design using genomics and proteomics, *Trends in Biotechnology*, 19, 181-185 (2001)). We believe that our nanostructured devices will be easily integrated into systems such as those being currently developed for interfaces between microfluidic separation devices and chemical detection components.

BRIEF SUMMARY OF THE INVENTION

The present disclosure describes an inventive method for separation of molecules in at least one nanochannel by providing at least two charged nanochannel walls; providing an electrolyte solution; introducing a mixture of at least two different types of molecules into the channel; electrophoresing the mixture of molecules; and allowing electroosmosis to electrokinetically transport at least one of the at least two molecule types.

Accordingly, an additional step comprises allowing the nanochannel walls to create an electrical double layer. Further, in the step of allowing electroosmosis to electrokinetically transport at least one of the at least two molecule types there may be the additional step of allowing differential distribution of the types of molecules across the electrical double layer. As a result, different electrokinetic velocities may result in response to the electrical double layer.

There may be the further step wherein the at least two different types of molecules exhibit differential adsorption to the at least two charged nanochannel walls.

Also, in the step of electrophoresing the mixture of molecules, the at least two different types of molecules exhibit different velocities.

Additionally, the at least two different types of molecules may exhibit differential entry into the nanochannel and can be one or more of a group consisting of organic molecules, dyes, amino acids, peptides, proteins, nucleic acids, saccharides, disaccharides, oligosaccharides, polysaccharides, hormones, and complexes thereof.

The at least one nanochannel can be a nanotube, and further, it can have a dimension gradient.

There can be further additional steps of applying a pressure gradient, detecting separation by fluorescence, detecting separation by spectroscopy, and/or detecting separation by electrochemistry.

The nanochannel walls can have at least one chemical functionality which exhibit chemical interactions selected from the group consisting of increasing activity, decreasing activity, or specific interaction with one or more of the at least two types of molecules.

There can be additional steps of allowing molecular interactions or reactions between at least one of the at least two types of molecules and electrolyte and/or between at least two of the at least two types of molecules.

Entry into a nanochannel can be determined by size of the at least two types of molecules, and in the step of allowing molecule types to travel along the at least one nanochannel at different electrokinetic velocities in response to the electrical double layer, the electrical double layer can be used to focus specific molecules to a region of fastest electrokinetic flow.

DESCRIPTION OF A PREFERRED EMBODIMENT

Figure 1A:
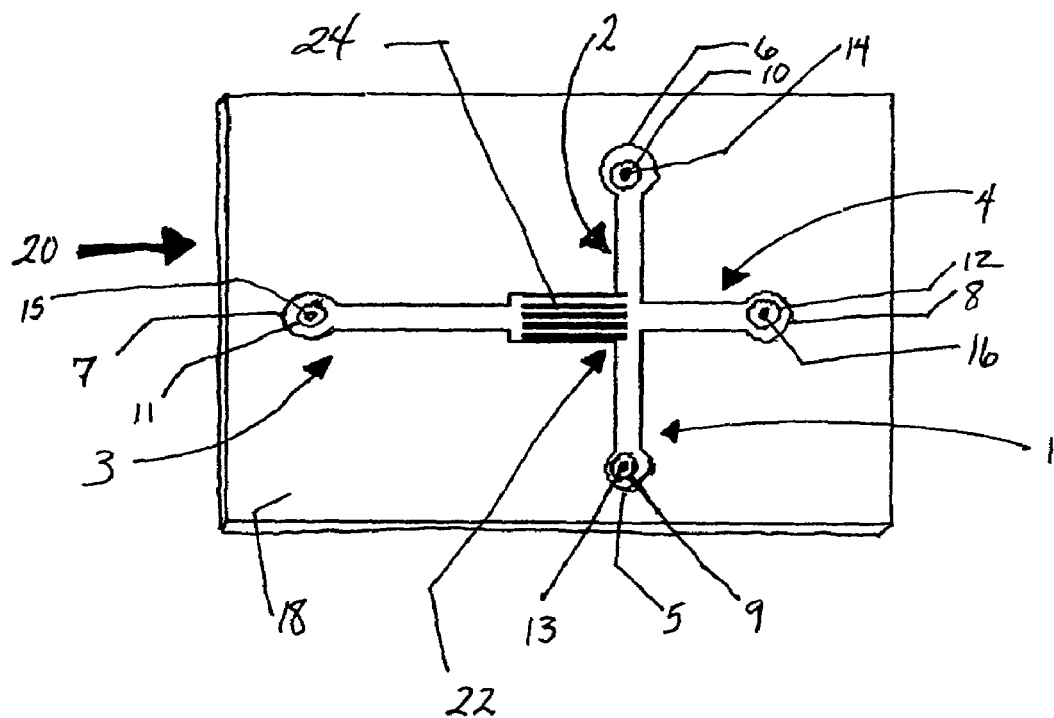
FIG. 1A is a top view schematic of the inventive integrated chip.

Nanoconfinement and nanofluidics, for the purposes of the invention, can be defined as a situation in which electrical double layers that form in the presence of charged channel walls (Gouy-Chapman layers) extend into the channel to a significant extent, thus representing a significant percentage of the channel width, and thereby affecting the nature of the electroosmotic velocity profiles.

In such channels, electroosmotic velocity profiles are not "plug" shaped as are typically observed in capillaries of larger sizes (See A. T. Conlisk, et al., *Analytical Chemistry* 74 2139 (2002)). While it may be impossible, even with near-field techniques, to observe such velocity profiles directly through particle velocimetry measurements, one might hope to see consequences of this non-plug flow by monitoring the convective axial dispersion of a dye. The Peclet number (vd/D) for a molecular dye with a diffusion coefficient (D) of ~$10^{-6}$ cm$^2$/s, an electroosmotic velocity (v) of tens of μm/s and a channel width of 100 nm, is very small (~$10^{-2}$). Thus one might expect that inference of velocity profiles by measurement of such axial dispersion would not be possible because of the fast diffusion of dyes in the radial direction.

We hypothesized that the electrostatic charge on nanochannel walls could significantly affect the distribution of charged molecular species within the nanochannel, thus having a significant impact on their electrokinetic transport. Therefore, we have demonstrated unique transport characteristics of charged molecules that are dissolved in electrolyte solutions and are electrokinetically pumped through channels with nanoscale widths. Such effects may have significant technological implications because most biomolecules (DNA, proteins, peptides) are charged, or can be complexed with charged surfactant molecules. The significant alteration of these species' mobility in electrokinetic and pressure-driven flows in channels of nanoscopic widths will enable efficient separations over short (hundreds of µm to cm) lengths not possible at macroscopic or even microscopic scales of channel widths.

The preferred apparatus of the invention is known in the art as a "T-chip" as shown in FIG. 1. The T-chip 20 utilized for the invention comprises four arm extensions 1,2,3,4 radiating at 90° angles from an internal intersection 22. Each external end 5,6,7,8 of arms 1,2,3,4, respectively, comprises a well, 9,10, 11,12, respectively. Electrodes 13,14,15,16 are inserted into wells 9,10,11,12 through a roof 18 of chip 20. The preferred roof material is Pyrex®, although other roof materials known in the art may be utilized. The preferred electrodes are comprised of platinum, although other electrodes known in the art may be utilized. Electrode 14 in well 10 of arm 2 is grounded, and the remaining three electrodes, 13,15,16, are attached to three independent DC power supplies' common ground. Chip 20 is then filled with buffer (any electrolysis buffer known in the art may be utilized) via capillary action from well 11 of arm 3. Chip 20 is then placed under an upright, laser-scanning confocal microscope and a mixture of at least two biomolecular materials (such as, but not limited to DNA, protein, peptides, or other charged materials or materials complexed with charged materials) is introduced into well 9 of arm 1. Electrode 13 is activated (preferably to approximately +10V) and electrodes 15 and 16 remain inactivated (set to 0V). The mixture will then move to microchannel towards intersection 22 by electroosmosis. Once the mixture reaches intersection 22, electrode 13 is inactivated (set to 0V) and electrode 16 is activated (set to approximately +30V), causing the mixture to begin movement towards external end 7 of well 11 of arm 3, through nanochannel section 24. More than one nanochannel section may be utilized.

We observed effects of electrokinetic transport of fluorescent dyes in nanochannels using such a silicon-based T-chip that integrates a nanochannel array with microfluidic injection ports 26 (FIG. 1B) (See M. J. O'Brien, et al., *J. Vac. Sci. Technol. B* 21 2941 (2003)). Such chips are well-suited for studying nanofluidic electrokinetic phenomena because: (1) their manufacture is reproducible, (2) they allow observation of channels that are nanoscopic in the plane of the chip, while being deep enough to allow significant molecular throughput and fluorescence detection, (3) they allow controlled introduction of analyte to the nanochannel array, and (4) $SiO_2$ and glass, which comprise the surfaces of the nanochannels, have native silanol groups which deprotanate in aqueous solutions providing the surface charge necessary for establishing the double layers that engender electroosmotic flow. Details of the chip fabrication, accomplished by a combination of conventional optical lithography and interferometric lithography is known in the art (See M. J. O'Brien, et al., *J. Vac. Sci. Technol. B* 21 2941 (2003)). The nanochannel section (preferably consisting of ~2000 parallel nanochannels or other configurations known in the art) is located within designated Arm 3 (as labeled in FIG. 1A), begins at the intersection of the channels, and extends approximately 1 cm down the channel (away from the intersection). A scanning electron micrograph of the cross section highlighting the nanochannel section in one of the chips used for this study is shown in FIG. 1B. These channels are between approximately 50 nm and approximately 200 nm wide by between approximately 500 nm and 800 nm deep, and have a pitch of between approximately 200 nm and approximately 400 nm or other configurations known in the art. The width of these channels is sufficient to allow interaction between the double layers extending from the channel walls.

The effects of the charge of the dyes were quantified by the observation of their electrokinetic transport in nanochannels. A solution of 1/100 dilution standard Tris/glycine electrophoresis buffer (0.24 mM Tris hydroxyl methane hydrochloride and 1.92 mM glycine, pH 8.8) was prepared to yield an ionic strength of ~0.35 mM (the respective pKa for each salt was used to estimate this value of ionic strength). The buffer was filtered through a 0.2 µm filter to remove particulate contaminants and then degassed under vacuum for at least three hours to reduce outgassing after the application of an electrical potential. Solutions of dyes (rhodamine B and Alexa 488 maleimide, Molecular Probes, Inc.) were prepared in this buffer at a concentration of 5 mg/mL. The addition of Alexa to the system was accounted for when we determined the total ionic strength, however its contribution was not significant. At this pH, rhodamine B (MW=479 Da) is neutral and Alexa 488 maleimide (MW=720 Da) has a −2 molecular charge (See http://www.probes.com/).

Platinum electrodes were inserted into wells (Nanoports, Upchurch Scientific Inc.) attached to the Pyrex roof. The holes in the roof provided access to the microfluidic channels. Electrode 14 (see FIG. 1A) was grounded, while the remaining three electrodes were attached to three independent DC power supplies' common ground. The chip was filled with buffer via capillary action from well 11 and placed under an upright, laser-scanning confocal microscope (Axioskop using an LSM5 scanning head, Zeiss, Inc.). Ten µL of a 1:1 mixture of the two dyes was introduced into well 9, and the electrode was set to approximately +10 V (electrodes 3 and 4 were set to 0V). The mixture was moved through the microchannel towards the intersection by electroosmosis. Separation of the two dyes was not observed in the microchannels. After the dye mixture reached the intersection, Electrode 13 was set to 0V and Electrode 4 was set to approximately +30V. The mixture began to move towards well 11, through the nanochannel section.

Figure 2:
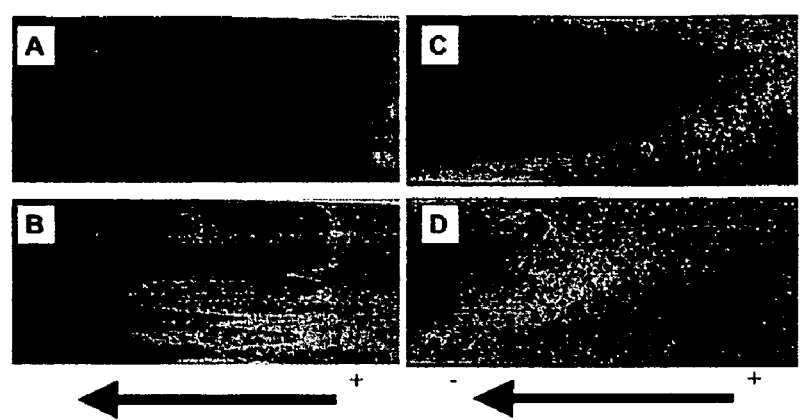
FIG. 2A is a two color fluorescence micrograph (green=Alexa 488, red=rhodamine B) showing separation of the dyes at the inlet of the nanochannels (each micrograph represents a 2.1 mm×1 mm section of the nanochannel array)
FIG. 2B is the fluorescence micrograph of FIG. 2A at approximately 50 nm in width at time, T=0 and T=30 seconds.
FIG. 2C is the fluorescence micrograph of FIG. 2A at approximately 200 nm in width at time, T=0.
FIG. 2D is the fluorescence micrograph of FIG. 2A at T=25.2 seconds.

To illustrate the phenomena of electrokinetic separation in nanochannel arrays, FIG. 2 depicts pseudo-colored fluorescence micrographs that show differential transport of two dyes in channels ~50 nm in width and in channels ~200 nm in width. The dye front propagated less uniformly in the 50 nm channels than in the larger channels, probably because the relative deviation in the width of the channels across the nanochannel array became more significant with decreasing channel size. A higher voltage was needed to introduce the Alexa dye into the nanochannel array than was needed to introduce the uncharged rhodamine dye. However, separation occurred almost immediately after the dyes entered the nanochannels.

We observed the effects of increasing the overlap of the electrical double layers by decreasing the width of the nanochannels, while keeping the ionic strength constant. It should be noted that, in principle, it is possible to qualitatively achieve a similar objective by changing the ionic strength of the buffer, however the range is limited due to practical restrictions. We conducted experiments using channels approximately 35 nm, 50 nm, 90 nm, 160 nm, and in 200 nm width, at voltage ranging from 0 to 150 volts. In all cases an approximately linear relationship was observed in which a higher imposed electric field resulted in faster transport of the dyes. Furthermore, the ratios of the velocities of the two dyes were found to be relatively independent of the imposed electric field, which is as expected (See A. P. Thompson, *J. Chem.*

*Phys.* 119 7503 (2003)). In the discussion below, we report the ratios of the velocities of the dyes to eliminate uncertainty in the voltage across the nanochannel array and thus to allow direct comparison with theory. Dye velocities were obtained by tracking the propagation of the dye fronts through the nanochannel array. Least squares linear regression was used to fit a line to the experimental data to obtain the relationship between voltage and dye velocity.

Figure 5:
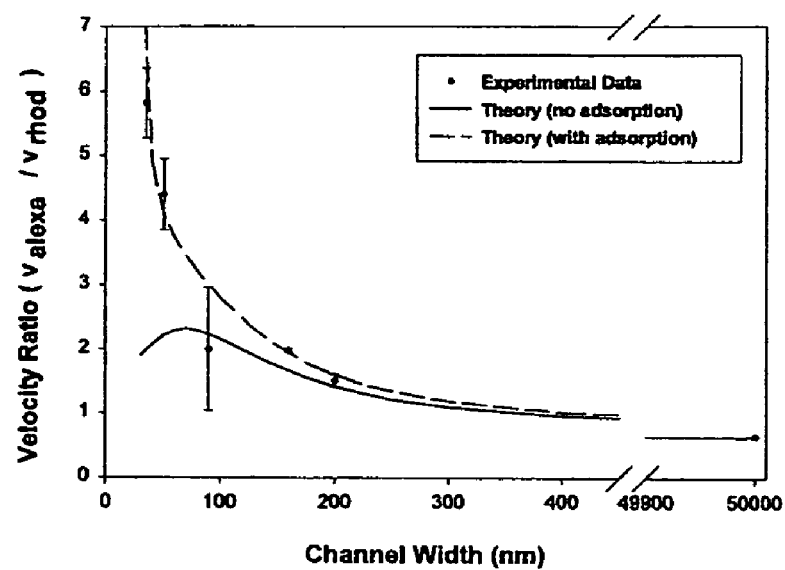
FIG. 5 is a line graph depicting theoretical and experimental ratios of velocities of dyes ($v_{Alexa}/v_{Rhod}$) versus width of the nanochannel. The experimental ratio is the ratio of the slopes of lines obtained by least squares linear regression of dye velocity versus applied voltage. Error bars are typically obtained by propagating the standard deviation from velocities obtained at five different voltages.

As the size of the channel decreased from 200 nm to 35 nm, the ratio of the velocities of the dyes increased from 1.5:1 to 5.8:1, as seen in FIG. 5. This behavior is opposite to that observed (and predicted) (See A. P. Thompson, *J. Chem. Phys.* 119 7503 (2003)) for electrokinetic transport of the dyes in larger scale channels (e.g., those used in conventional microchip capillary electrophoresis). In such experiments we have observed that the negatively charged Alexa dye lags behind rhodamine because the electrophoretic force, which is experienced only by the charged dye, acts counter to the electroosmotic flow.

In the sections below, we present an analytical model that describes three phenomena that impact dye transport through the nanochannels, electroosmosis, electrophoresis of the charged dye, and adsorption of the neutral dye to the nanochannel walls.

Electrokinetic Theory

A significant difference between fluidics in nanochannels and conventional electrophoretic capillaries (or microfluidic electrokinetic devices) is in the fact that the channel widths can be comparable to the thickness of the double layers that develop at the walls (See W. B. Russel, et al., *Colloidal Dispersions* (*Cambridge University Press*, 1989)). In fact, at small enough scales, important dimensions such as the Debye screening length, channel width, and the diameters of biological species become of the same order. Described here is an approximation that allows for analytical treatment of the electrokinetics in such channels due to electroosmosis and electrophoresis, assuming a two-dimensional flow field in channels with parallel walls and weak double layer overlap.

When the double layers do not overlap substantially, one may assume that the total electric potential between the walls of the nanochannels equals the sum of the potentials of single walls (See E. J. Verwey and J. T. Overbeek, *Theory and Stability of Lyophobic Colliods.* (*Elsevier Amsterdam*, 1948)). Therefore the dimensionless potential distribution across an individual nanochannel can be given as:

$$\Psi(x) = 4 \left[ \begin{array}{l} \tanh^{-1}\left(\tanh\left[\frac{z_e e \zeta}{4kt}\right] \exp(-\kappa x)\right) + \\ \tanh^{-1}\left(\tanh\left[\frac{z_e e \zeta}{4kt}\right] \exp(-\kappa(d-x))\right) \end{array} \right]. \quad \text{Equation 1}$$

This approximation is valid for an arbitrarily high surface potential but requires weak overlap ($Kd \geqq 2$) of the double layers (See Q. S. Pu, J. S. Yun, H. Temkin, S. R. Liu, *Nano Letters* 4 1099 (2004))). Here $z_e$ is the charge number of the background electrolyte, d is the nanochannel width, $\zeta$ is the electrokinetic (zeta) potential of the nanochannel walls, and $K=[2e^2z^2C_{el}/(kT\epsilon_0\epsilon)]^{1/2}$ is the Debye screening parameter, in which e is the unit charge, z is the valence of the background electrolyte and $C_{el}$ is its number concentration, $\epsilon_0$ is the dielectric permittivity of free space, $\epsilon$ is the relative dielectric constant of the solvent and kT is the thermal energy. Using Equation (1), we can derive an expression:

$$v_{eo}(x) = \epsilon\epsilon_0 E \zeta/\eta)[1-\psi(x)/\zeta] \quad \text{Equation 2.}$$

for the electroosmotic velocity profile (See Q. S. Pu, J. S. Yun, H. Temkin, S. R. Liu, *Nano Letters* 4 1099 (2004)). The average velocity across a channel is given by:

$$\bar{v}_{eo} = \frac{1}{d}\int_0^d v_{eo}(x)dx = \frac{\epsilon\epsilon_0\zeta E}{d\eta}\int_0^d \left[1 - \frac{\Psi(x)}{\zeta}\right]dx. \quad \text{Equation 3}$$

where $\eta$ is the solvent viscosity. The concentration distribution of a species across the nanochannel is $C(x)=C_0 \exp[-z_A e \psi(x)/kt]$ where $C_0$ is the concentration of the species in the microchannel feeding the nanochannel array. Then the average concentration is:

$$\bar{C} = \frac{C_o}{d}\int_0^d \exp\left[-\frac{z_A e \Psi(x)}{kt}\right]dx. \quad \text{Equation 4}$$

The uncharged dye is electrokinetically transported along the nanochannel by electroosmosis only, at a velocity given by Equation (2). Solving Equation (2) for the zeta potential using the velocity of rhodamine B measured for the 200 nm nanochannels ($v_{eo}=3.26\times10^{-5}$ m/s) we obtain $\zeta=80.7$ mV. This value of the zeta potential was used in estimation of dye velocities for all other nanochannel sizes because we assumed that the effect of adsorption of rhodamine B is small at this width (vide infra).

Modeling the movement of the negatively charged dye is more complicated since it will distribute between the negatively charged nanochannel walls non-uniformly, tending to segregate towards the center of the channel. Also it will tend to be excluded from entering the nanochannels because of the higher electrochemical potential inside the channel. If however, the convective electroosmotic flow is strong enough, the dye will be forced into the channel. Once it is inside, the negatively charged dye will travel along the nanochannel driven by electrokinetic forces. The effective (concentration weighted) electrokinetic velocity profile of a dye in the nanochannel is given by Equation (5).

$$v(x) = \frac{C(x)v_{eo}(x)}{\bar{C}} - v_{ep}. \quad \text{Equation 5}$$

Figure 3:
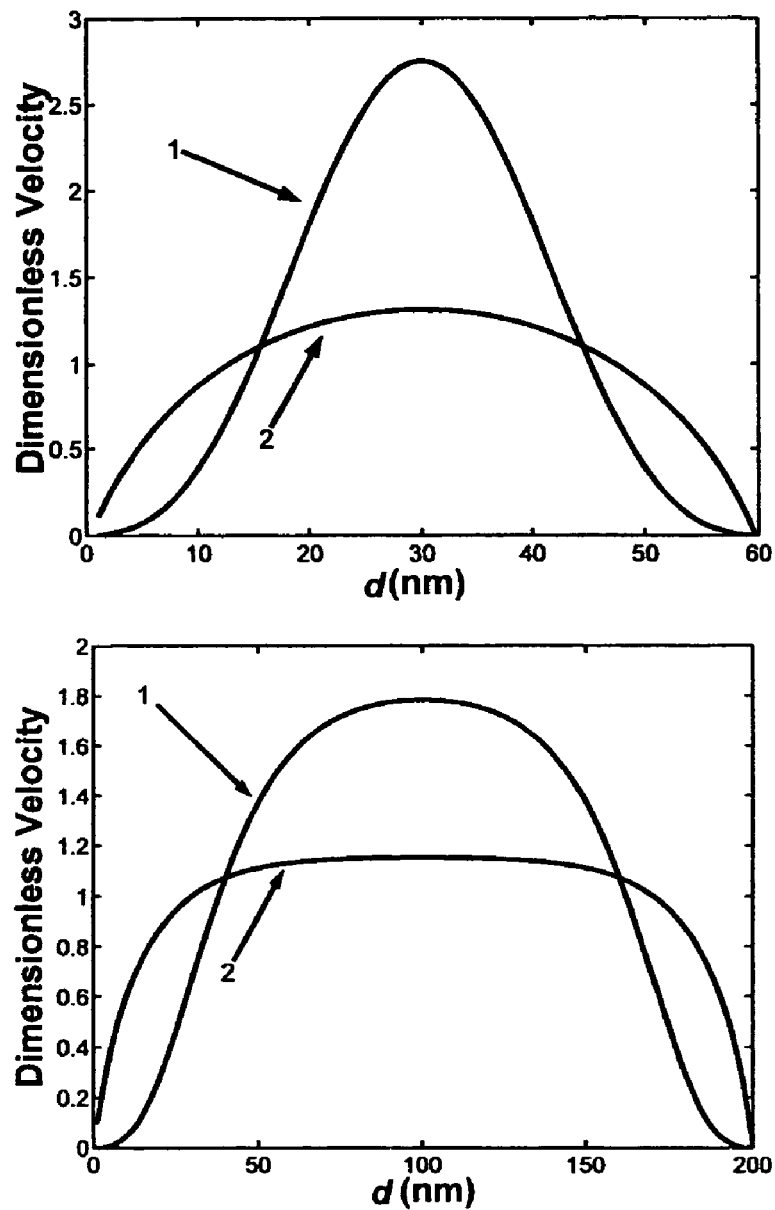
FIG. 3 is a line graph depicting dimensionless electroosmotic velocity for $[c(x)v_{eo}(x)/\overline{cv}_{eo}]$ for charged (1) and $[v_{eo}(x)/\overline{v}_{eo}]$ uncharged (2) analytes as a function of the channel position in a 60 nm (top) and 200 nm (bottom) channel.

FIG. 3 shows the effective electroosmotic velocity distribution of the two dyes derived from equation (4) for two nanochannel sizes, 200 nm and 60 nm. At the maximum of the distribution, for the 200 nm wide channels, the velocity for the charged species is 1.78 times that of the electroosmotic fluid flow rate defined by Equation (2). For uncharged analytes, the velocity is assumed to be about the same as the electroosmotic flow rate, neglecting adsorption. Equation (4) predicts that the greatest difference in the maximum electrokinetic velocities will be observed at approximately 60 nm (see FIG. 3); below this width the extent of double layer overlap starts hindering the development of the electroosmotic velocity profiles such that less difference in dye velocities are predicted. In the discussion below (and FIG. 5), the ratios of the maximum dye velocities predicted include the electrophoretic effect expected for the negatively charged dye.

Adsorption

Figure 4:
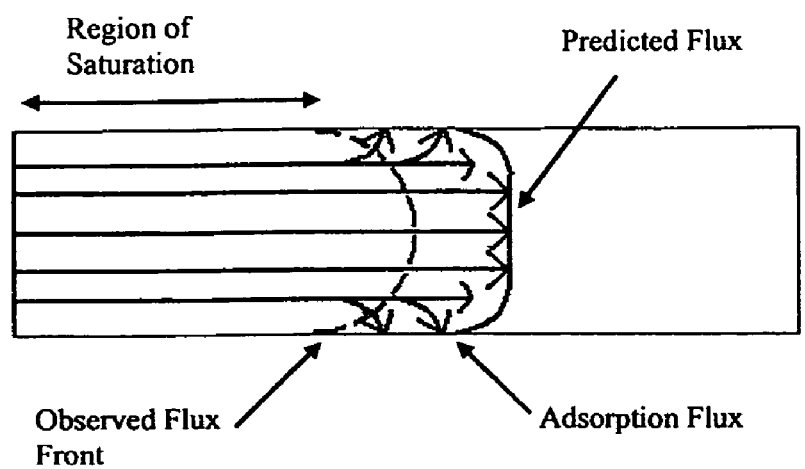
FIG. 4 is a schematic illustration of how adsorption may produce a lower measured velocity for a plug of a species that is distributed along the width of a nanochannel.

In addition to the separation effects due to electrokinetic flow, the adsorption of the neutral dye to the channel walls can increase the separation observed in these nanoscale channels. The charged Alexa dye is electrostatically repulsed from the nanochannel walls. A portion of the neutral rhodamine B molecules, in a nanochannel, is diverted toward the walls, thus depleting the dye front. This reduces the net forward flux and manifests itself as an overall slower velocity. However, the effect of adsorption is not negligible when the channel width, and therefore the amount of dye in the channels, becomes small (See G. Drazer, *Phys Rev Lett.* 89 244501. (2002)). The amount of neutral dye that is adsorbed by the walls should remain about the same, for each nanochannel width, because the area of the channel walls changes only slightly for the high aspect ratio channels. However, the total amount of dye in the channel will decrease substantially as the volume of the channel decreases. Thus, as the channel width decreases, adsorption reduces the flux of the neutral dye along the channel to a greater extent. A schematic representation of how this adsorption phenomenon affects the flux of neutral species is presented in FIG. 4.

Equation (6) was used to calculate the ratio of the maximum velocities of the charged and the neutral dyes, taking into account electroosmosis, electrophoresis, and adsorption.

$$\frac{v_{charged}}{v_{neutral}} = \frac{j_{charged} - j_{electrophoresis}}{j_{neutral} - (c_{adsorption}/d)}$$

Here $j_{charged}$ is the electroosmotic flux of the charged species, $j_{neutral}$ is the electroosmotic flux of the neutral species, and $c_{adsorption}$ is a constant representing the adsorption properties of the channel walls). The electrophoretic flux, $j_{electrophoresis}$, was measured by electrokinetically pumping these two dyes within a microchannel of known width (50 μm).

A plot of the theoretical ratio of velocities with adsorption and without adsorption (along with the experimentally measured ratios) as a function of channel width is given in FIG. 5. Using this plot we are able to estimate a crossover channel width of roughly 400 nm, below which the flux of the negatively charged species becomes greater than the flux of the neutral species. In channels larger than the crossover width, as typical in microscale electrophoretic systems, neutral species move faster than negatively charged species because the charged species will be slowed by their electrophoretic drag.

Separation of the dyes was also achieved by applying a pressure gradient to drive the fluid in the channels (data not shown). Again, the negatively charged Alexa dye is repelled by the negatively charged channel walls, toward the center of the channels, while the uncharged rhodamine dye was more uniformly distributed along the width of the channel. Because of the parabolic velocity profile expected for pressure driven flow, fluid in the center portion of the channel travels faster than the rest of the fluid (See J. T. Cheng, N. Giordano, *Physical Review E* 65 031206 (2002); K. P. Travis, K. E. Gubbins, *J. Chem. Phys.* 112 1984 (2000)). Also, adsorption of the neutral dye will again slow its net forward velocity. Thus separations can be achieved because of the difference in dye velocities.

We have shown that when fluidic systems approach the size of the electrical double layer, separation phenomena are observed that differ from those typical of larger systems. Spatially averaged electrokinetic transport in these nanoscale channels can effectively be observed by confocal scanning laser microscopy. The experimentally obtained data agrees reasonably well with the continuum-based analytical model developed. Further refinement of the model will take into account the shape of the channel cross section. Under the ionic strength conditions of this study, the electrokinetic model is expected to remain valid in channels wider than approximately 32 nm, at which point the assumption of weak double layer overlap would not be expected to hold. The use of nanoconfined electrokinetic transport has proven effective to perform molecular separations, quantified here by the ratio of dye velocities. As the size of the channels decreases, the ratio of the velocity of negatively charged to that of uncharged species increases. We have also begun to quantify, as shown below, the effectiveness of pressure driven separations of these species, and to investigate other molecular species including peptides, proteins and DNA.

Protein Separation

Preliminary experiments have integrated nanofluidic architectures fabricated by the lithographic patterning and bonding methods into microfluidic systems that have been used recently to develop protein separation strategies. 10 We focused on microfluidic systems formed by conventional optical lithography and pattern transfer methods (because of ease of availability, although other lithography and transfer methods are anticipated as viable) and we developed methods to incorporate and interface nanofabricated separation matrices with these microfluidic systems. The cells had the following characteristics: (1) electrochemical current and fluid flow must be restricted to occur only through the separation matrix; (2) loading and stacking functions were included; and (3) monitoring of mobility and biomolecular detection was possible (e.g., through fluorescence imaging, although other methods known in the art could be utilized).

Figure 1B:
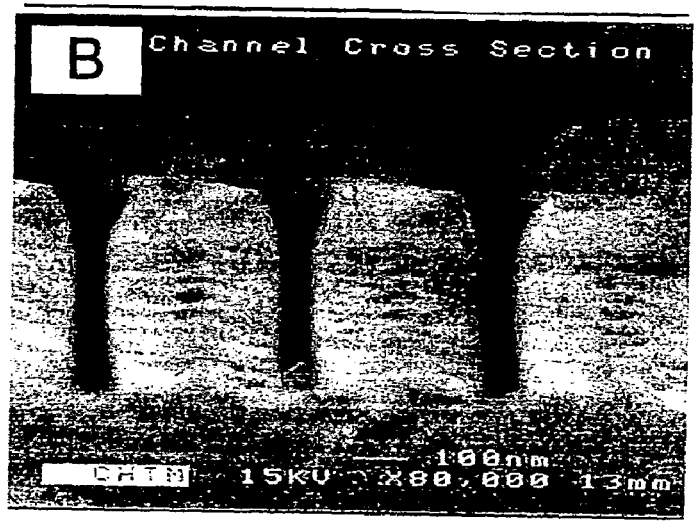
FIG. 1B is an cross section SEM image of the nanochannel section of the chip of FIG. 1.

An example of the most basic design is FIG. 1A-B. In this design, the microfluidic components, usually comprising a cross section of around approximately 50 to approximately 100 μm, are used to interface with external fluid and sample supplies, electrodes (for electrophoresis or endo-osmotic pumping), and pumps and to deliver fluorescently labeled molecules to (and in certain cases, stack them at) the entrance of the nanostructured separation matrix. All these interfaces are accomplished by methods known commonly in the art. Gas bubbles that evolve at the electrode surfaces can be restricted from entering the separation system by distance or by a hydrogel membrane. Initially we will investigate electrophoretic mobility of different molecules through simple types of nanostructured matrices, for example, parallel nanochannels of less than 100 nm width and arrays of nanoposts with interpost separation of less than 100 nm. Our preliminary investigations into electrokinetic mobility within nanochannels has demonstrated that the effects of electrophoresis, electro-osmosis and possible chemical interactions originating from the walls more complex than originally envisioned. Our first set of investigations utilized fluorescent dyes of different molecular weights and charge in order to investigate the interactions. However, it will be clear to one versed in the art, given our invention, that other charged molecules could be substituted for the dyes utilized, therefore effecting separation of important charged molecules by these nanoscale fluidic channels.

What is claimed is:

1. A method for separation of molecules in at least one nanochannel comprising:
   providing at least one nanochannel having charged nanochannel walls;
   providing an electrolyte solution to the at least one nanochannel so that an electrical double layer forms near the charged nanochannel walls;
   introducing a mixture of at least two different types of molecules into at least one nanochannel;

allowing electroosmosis through at least one nanochannel to transport at least one of the at least two molecule types within the nanochannel and to separate at least two different types of molecules within the nanochannel.

2. The method of claim 1, wherein the step of allowing electroosmosis to transport at least one of the at least two molecule types comprises the additional step of allowing differential distribution of the types of electrolytes and/or molecules across the electrical double layers.

3. The method of claim 1, wherein an additional step comprises allowing molecule types to travel along the at least one nanochannel at different electrokinetic velocities in response to the electrical double layers.

4. The method of claim 3 wherein in the step of allowing molecule types to travel along the at least one nanochannel at different electrokinetic velocities in response to the electrical double layer, the electrical double layer is used to focus specific molecules to a region of fastest electrokinetic flow.

5. The method of claim 1 comprising the additional step wherein the at least two different types of molecules exhibit differential adsorption to the at least two charged nanochannel walls.

6. The method of claim 1, wherein in the step of allowing electroosmosis to transport and separate the molecules, the at least two different types of molecules exhibit different velocities.

7. The method of claim 6, wherein electrophoresis contributes to the different velocities and the separation of the molecules.

8. The method of claim 1 wherein the at least two different types of molecules exhibit differential entry into the nanochannel.

9. The method of claim 1 wherein the at least two different types of molecules comprise the group consisting of organic molecules, dyes, amino acids, peptides, proteins, nucleic acids, saccharides, disaccharides, oligosaccharides, polysaccharides, hormones, and complexes thereof.

10. The method of claim 1 wherein the at least one nanochannel comprises a nanotube.

11. The method of claim 1 comprising the additional step of applying a pressure gradient.

12. The method of claim 1 comprising the additional step of detecting separation by fluorescence.

13. The method of claim 1 comprising the additional step of detecting separation by spectroscopy.

14. The method of claim 1 comprising the additional step of detecting separation by electrochemistry.

15. The method of claim 1 wherein the nanochannel additionally comprises a dimension gradient.

16. The method of claim 1 wherein the nanochannel walls additionally comprise at least one chemical functionality.

17. The method of claim 16 wherein the method further comprises separation using chemical interactions by at least one of the at least two molecule types with the chemical functionality, wherein the chemical interactions are selected from the group consisting of increasing activity, decreasing activity, or specific interaction with one or more of the at least two types of molecules.

18. The method of claim 1 comprising the additional step of allowing molecular interactions or reactions between at least one of the at least two types of molecules and electrolyte.

19. The method of claim 1 comprising the additional step of allowing molecular interactions or reactions between at least two of the at least two types of molecules.

20. The method of claim 1 wherein entry into a nanochannel is determined by size of the at least two types of molecules.

21. A method for separation of molecules in at least one nanochannel comprising:
providing at least one nanochannel having charged nanochannel walls;
providing an electrolyte solution to the at least one nanochannel so that an electrical double layer forms near the charged nanochannel walls;
introducing a mixture of at least two different types of molecules into at least one nanochannel;
allowing electroosmosis through at least one nanochannel to transport at least one of the at least two molecule types within the nanochannel and to separate at least two different types of molecules within the nanochannel; and
detecting separation of at least two molecule types within the nanochannel.

22. A method for separation of molecules in at least one nanochannel comprising:
providing at least one nanochannel having charged nanochannel walls;
providing an electrolyte solution to the at least one nanochannel so that an electrical double layer forms near the charged nanochannel walls;
introducing a mixture of at least two different types of molecules into at least one nanochannel; and
applying a pressure gradient along at least one nanochannel to transport at least one of the at least two molecule types within the nanochannel and to separate at least two different types of molecules within the nanochannel.

* * * * *